(12) United States Patent
Schweikert et al.

(10) Patent No.: US 7,455,660 B2
(45) Date of Patent: Nov. 25, 2008

(54) LOCKING GUIDEWIRE STRAIGHTENER

(75) Inventors: Timothy Schweikert, Levittown, PA (US); Kevin Sanford, Chalfont, PA (US)

(73) Assignee: Medical Components, Inc., Harleysville, PA (US)

( * ) Notice: Subject to any disclaimer, the term of this patent is extended or adjusted under 35 U.S.C. 154(b) by 273 days.

(21) Appl. No.: 10/960,737

(22) Filed: Oct. 7, 2004

(65) Prior Publication Data

US 2005/0049572 A1    Mar. 3, 2005

Related U.S. Application Data

(63) Continuation-in-part of application No. 10/366,247, filed on Feb. 13, 2003, now abandoned.

(60) Provisional application No. 60/434,262, filed on Dec. 18, 2002.

(51) Int. Cl.
*A61M 5/00* (2006.01)
*A61M 31/00* (2006.01)
*A61M 25/00* (2006.01)
*A61B 5/00* (2006.01)

(52) U.S. Cl. .................. 604/171; 604/508; 600/585

(58) Field of Classification Search .............. 604/528, 604/523, 264, 158, 159, 27, 44, 164.01–164.13, 604/535, 538, 171; 600/585, 434
See application file for complete search history.

(56) References Cited

U.S. PATENT DOCUMENTS

| | | | |
|---|---|---|---|
| 4,205,675 A * | 6/1980 | Vaillancourt | 604/508 |
| 4,349,023 A | 9/1982 | Gross | |
| 4,799,496 A | 1/1989 | Hargreaves et al. | |
| 4,940,062 A | 7/1990 | Hampton et al. | |
| 5,002,535 A | 3/1991 | Gross | |
| 5,117,839 A | 6/1992 | Dance | |
| 5,125,905 A * | 6/1992 | Wright et al. | 604/171 |
| 5,191,888 A | 3/1993 | Palmer et al. | |
| 5,217,435 A | 6/1993 | Kring | |
| 5,263,938 A | 11/1993 | Orr et al. | |
| 5,267,955 A | 12/1993 | Hanson | |
| 5,273,042 A | 12/1993 | Lynch et al. | |
| 5,279,573 A * | 1/1994 | Klosterman | 604/171 |
| 5,282,478 A | 2/1994 | Fleischhaker, Jr. et al. | |
| 5,282,479 A * | 2/1994 | Havran | 600/585 |

(Continued)

*Primary Examiner*—Matthew F Desanto
(74) *Attorney, Agent, or Firm*—Anton P. Ness; Fox Rothschild LLP (57) ABSTRACT

A guidewire straightener assembly (50,200,300,400) including a guidewire tube (56,250,450) with a tubular passage therethrough having a first diameter and a distal end, optionally including a collar (58,260,462) having a second diameter larger than the first diameter. The assembly also includes a guidewire straightener (10,210,410) having a distal end (12, 212,412), a proximal end (14,214,414) having an exterior surface with a diameter sized to fit within the guidewire tube, and a longitudinal passageway (18,218,418) therethrough sized to accept the guidewire (52,202,402). The proximal end of the guidewire straightener further includes a biasing member (20,220,420) with at least one finger (26,216,416) therealong. The assembly further includes a guidewire (52,202,402) disposed within the tubular passage and the longitudinal passageway (18,218,418). When the guidewire straightener (10, 210,410) is disposed within the guidewire tube in a first position with its biasing member in the tubular passage, the at least one finger (26,216,416) is biased by the tubular passage into frictional engagement with the guidewire; when disposed in a second position, the at least one finger is disposed away from frictional engagement with the guidewire.

9 Claims, 12 Drawing Sheets

U.S. PATENT DOCUMENTS

| | | | |
|---|---|---|---|
| 5,290,247 A * | 3/1994 | Crittenden | 604/171 |
| 5,322,513 A * | 6/1994 | Walker | 604/161 |
| 5,360,403 A | 11/1994 | Mische | |
| 5,443,081 A | 8/1995 | Klosterman | |
| 5,546,958 A | 8/1996 | Thorud et al. | |
| 5,634,475 A | 6/1997 | Wolvek | |
| 5,634,897 A | 6/1997 | Dance et al. | |
| 5,831,666 A | 11/1998 | Palmer et al. | |
| 5,843,002 A | 12/1998 | Pecor et al. | |
| 5,851,189 A | 12/1998 | Forber | |
| 5,978,699 A | 11/1999 | Fehse et al. | |
| 6,030,349 A | 2/2000 | Wilson et al. | |
| 6,039,722 A | 3/2000 | Greive | |
| 6,139,540 A | 10/2000 | Rost et al. | |
| 6,193,706 B1 | 2/2001 | Thorud et al. | |
| 6,551,281 B1 | 4/2003 | Raulerson et al. | |
| 6,641,563 B1 | 11/2003 | Vitullo et al. | |
| 2004/0122416 A1 | 6/2004 | Schweikert et al. | |

\* cited by examiner

LOCKING GUIDEWIRE STRAIGHTENER

CROSS-REFERENCE TO RELATED APPLICATION

The present application is a Continuation-in-Part of U.S. patent application Ser. No. 10/366,247, filed on Feb. 13, 2003, now abandoned which claims priority from U.S. Provisional Patent Application Ser. No. 60/434,262, filed on Dec. 18, 2002.

FIELD OF THE INVENTION

The present invention relates to a catheter guidewire and a method of retaining a catheter guidewire in a guidewire tube.

BACKGROUND OF THE INVENTION

Catheter guidewires are used to facilitate introduction of a catheter into a patient. In a typical catheter installation, an insertion site is located, and an incision is made by the inserting physician at the insertion site. A syringe is inserted into the patient through the incision to locate the blood vessel, such as a vein, to be catheterized. A flexible metal guidewire is typically inserted through the syringe and into the blood vessel to further enable the inserting physician to insert the catheter into the patient. The guidewire typically has a "J-shaped" distal end, so as not to tear into the patient's blood vessel during insertion. The guidewire is quite flexible so that it can bend with the contours of the blood vessel, but the flexibility of the guidewire, along with the "J-shape", can make it difficult for the physician to insert the distal end of the guidewire into the syringe. Guidewire straighteners are used to straighten out the "J-shape" and to assist the physician in inserting the distal tip of the guidewire into the syringe for advancement into the blood vessel.

A guidewire is typically stored in a coiled plastic tube, both for ease of physician use and for sterility. However, during shipping, the guidewire can work its way out of the tube, making the guidewire more difficult to handle and potentially compromising the sterility of the guidewire.

A known guidewire straightener is disclosed in U.S. Pat. No. 5,125,905. This guidewire straightener utilizes a cantilevered extension at the proximal end of the straightener to grasp a guidewire and retain the guidewire in its tube. It is believed by the inventors that the prior art design does not provide sufficient gripping between the straightener and the guidewire. It is also believed by the inventors that the prior art design may be prone to breakage from fatigue.

It would be beneficial to provide a guidewire straightener that provides increased gripping between the straightener and the guidewire so that the guidewire does not work its way out of the tube, as well as a guidewire straightener that is less prone to breakage from fatigue.

BRIEF SUMMARY OF THE INVENTION

Briefly, the present invention provides a guidewire straightener assembly. The assembly comprises a guidewire tube including a tubular passage having a first diameter and a distal end including a collar having a second diameter, larger than the first diameter. The assembly also includes a guidewire straightener having a distal end, a proximal end having an exterior surface with a diameter sized to fit within the guidewire tube, and a longitudinal passageway sized to accept the guidewire, the passageway extending between the proximal end and the distal end. The assembly further includes a guidewire having a third diameter, smaller than the first diameter, wherein the guidewire is disposed within the tubular passage and the longitudinal passageway. The proximal end of the guidewire straightener further includes at least one finger extending therefrom such that, when the guidewire straightener is disposed within the guidewire tube in a first position in the tubular passage, the at least one finger is biased by the tubular passage into frictional engagement with the guidewire. When the guidewire straightener is disposed within the guidewire tube in a second position in the collar, the at least one finger is disposed away from frictional engagement with the guidewire.

The present invention also provides a catheter guidewire tube comprising a body having a distal end, a proximal end, and a tube passageway extending between the distal end and the proximal end, wherein the tube has a first diameter. The assembly also includes a collar fixedly connected to the distal end, wherein the collar comprises a longitudinal passage having a second diameter, larger than the first diameter, and wherein the collar further comprises a distal opening having a third diameter, smaller than the second diameter.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

In the drawings, like numerals indicate like elements throughout. Certain terminology is used herein for convenience only and is not to be taken as a limitation on the present invention. The words "proximal" and "distal" refer to directions away from and closer to, respectively, the insertion tip of the guidewire in the guidewire assembly according to the present invention. The terminology includes the words above specifically mentioned, derivatives thereof, and words of similar import. The following describes a preferred embodiment of the invention. However, it should be understood based on this disclosure, that the invention is not limited by the preferred embodiment described herein.

Figure 1:
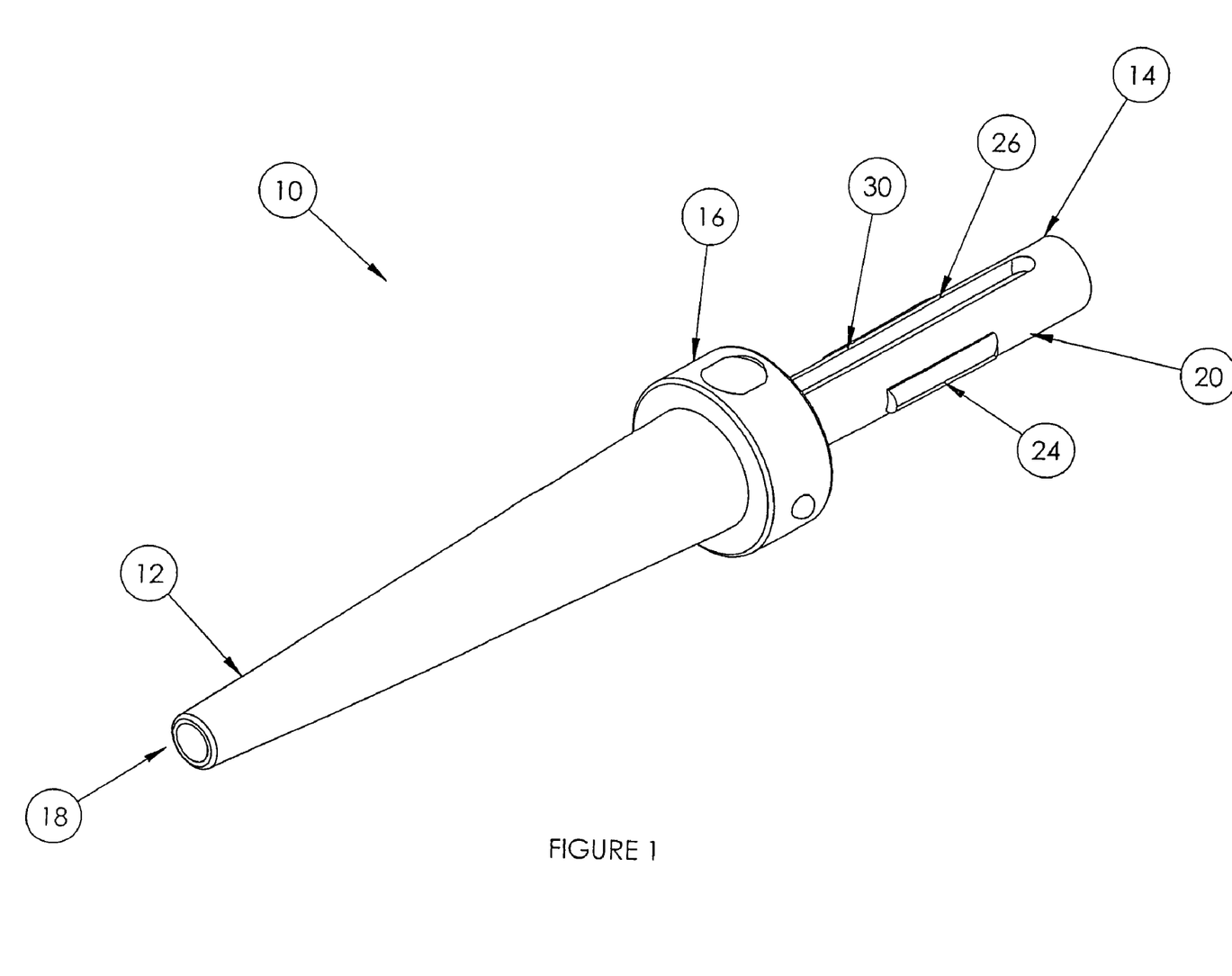
FIG. 1 is a perspective view of a catheter guidewire straightener according to an embodiment of the present invention.
Figure 2:
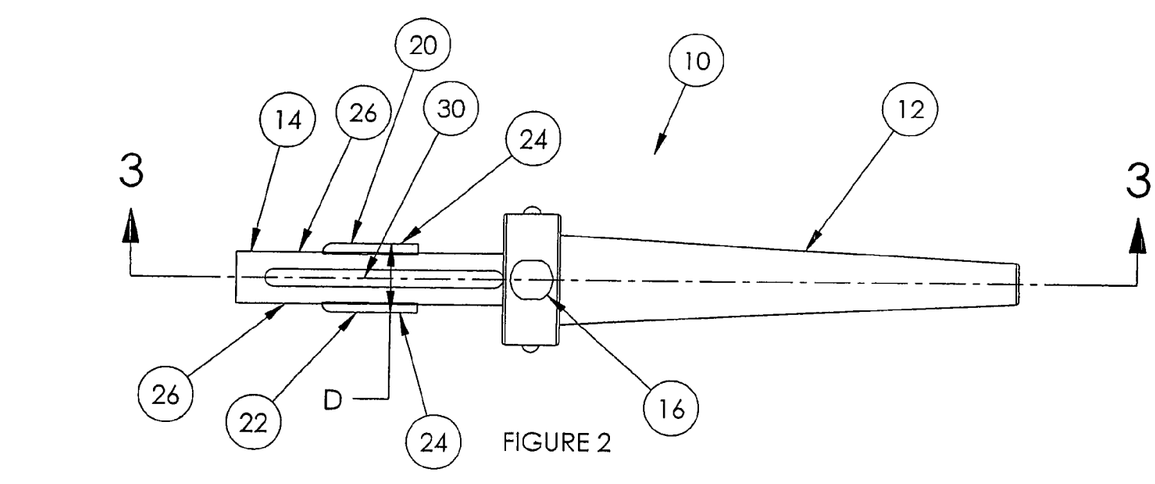
FIG. 2 is a side elevational view of the catheter guidewire straightener shown in FIG. 1.
Figure 3:
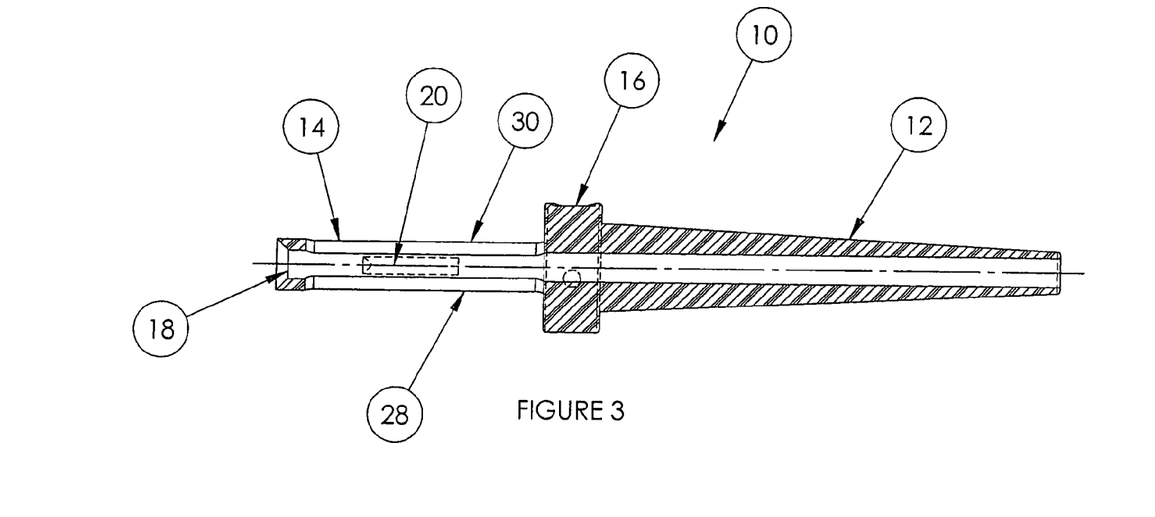
FIG. 3 is a sectional view of the catheter guidewire straightener taken along line 3-3 of FIG. 2.

A catheter guidewire straightener 10 according to an embodiment of the present invention is shown in FIGS. 1-3. The guidewire straightener 10 is comprised of a generally frusto-conically shaped distal end 12 and a generally cylindrically shaped proximal end 14. A stop collar 16 is disposed between the distal end 12 and the proximal end 14. A straightener passageway 18 extends through the guidewire straightener 10 between the distal end 12 and the proximal end 14. The straightener passageway 18 is sized to allow a guidewire 52, shown in a guidewire assembly 50 in FIG. 4, to pass through the straightener passageway 18 with little or no interference. A standard guidewire has a diameter of approximately 0.038 inches (approximately 0.97 mm), and the straightener passageway 18 has a diameter of approximately 0.05 inches (approximately 1.27 mm). Therefore, when the guidewire 52 is inserted into the straightener passageway 18, a clearance of approximately 0.012 inches (approximately 0.30 mm) is provided between the guidewire 52 and the guidewire straightener 10.

Referring back to FIGS. 1-3, the proximal end 14 of the straightener 10 includes first and second diametrically opposed biasing assemblies 20, 22, which are each comprised of a lug 24 disposed on a biasing member 26, such as a leaf spring. A distance between free ends of each lug 24 on the biasing assemblies 20, 22, as shown in FIG. 2, is defined as a diameter "D".

Each biasing assembly 20, 22, extends longitudinally along the proximal end 14 of the straightener 10, with channels 28, 30 disposed on either side of the biasing assemblies 20, 22. The channels 28, 30 allow the lugs 24 and the biasing members 26 to deflect toward the straightener passageway 18 when force is applied on the lugs 24 toward the straightener passageway 18. The biasing members 26 resist such force and bias the lugs 24 away from the straightener passageway 18.

Preferably, the guidewire straightener 10 is constructed from a polymer, such as polypropylene, although those skilled in the art will recognize that other, suitable materials may be used.

Figure 4:
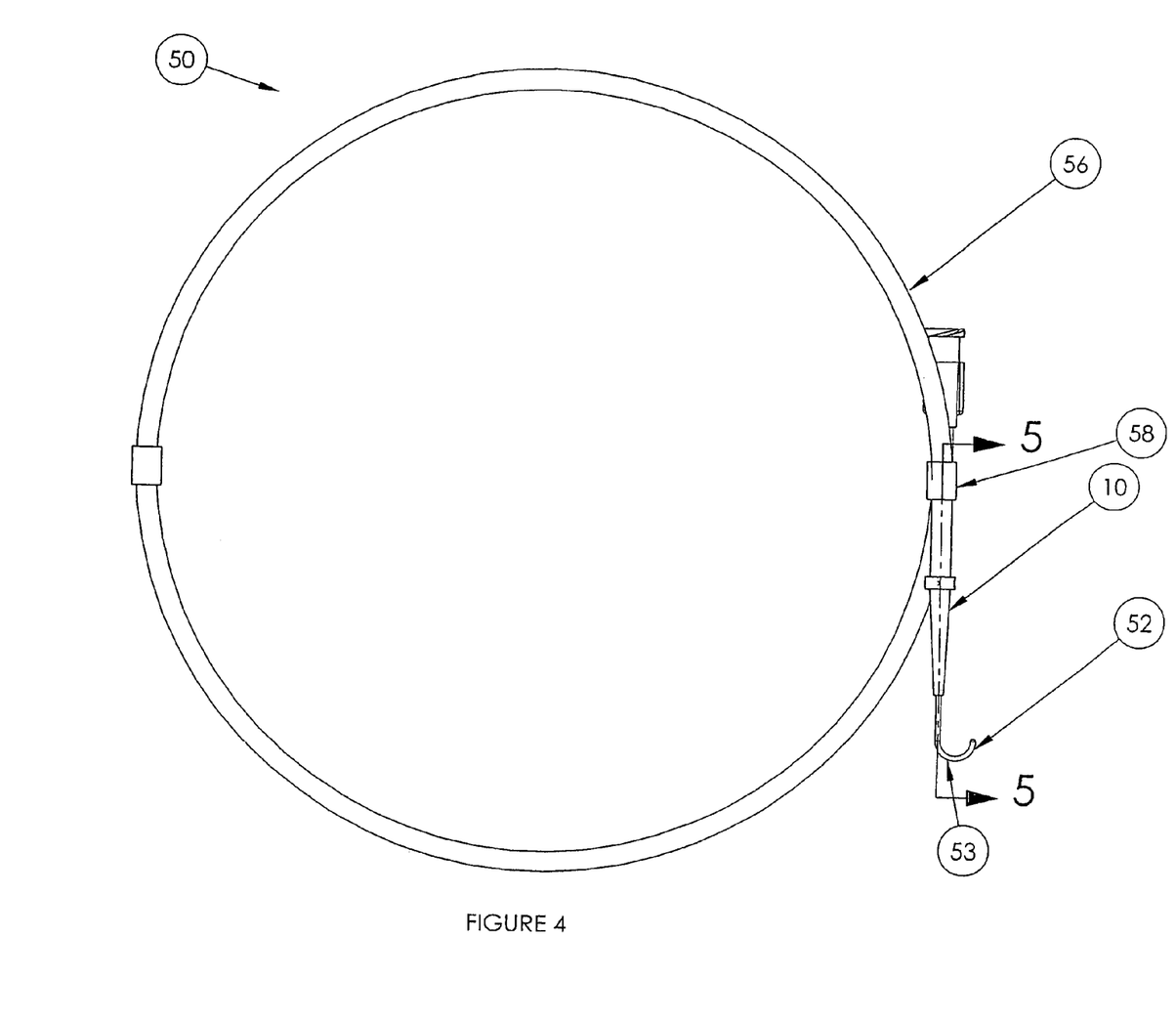
FIG. 4 is a plan view of a catheter guidewire assembly incorporating the catheter guidewire straightener shown in FIGS. 1-3.
Figure 5:
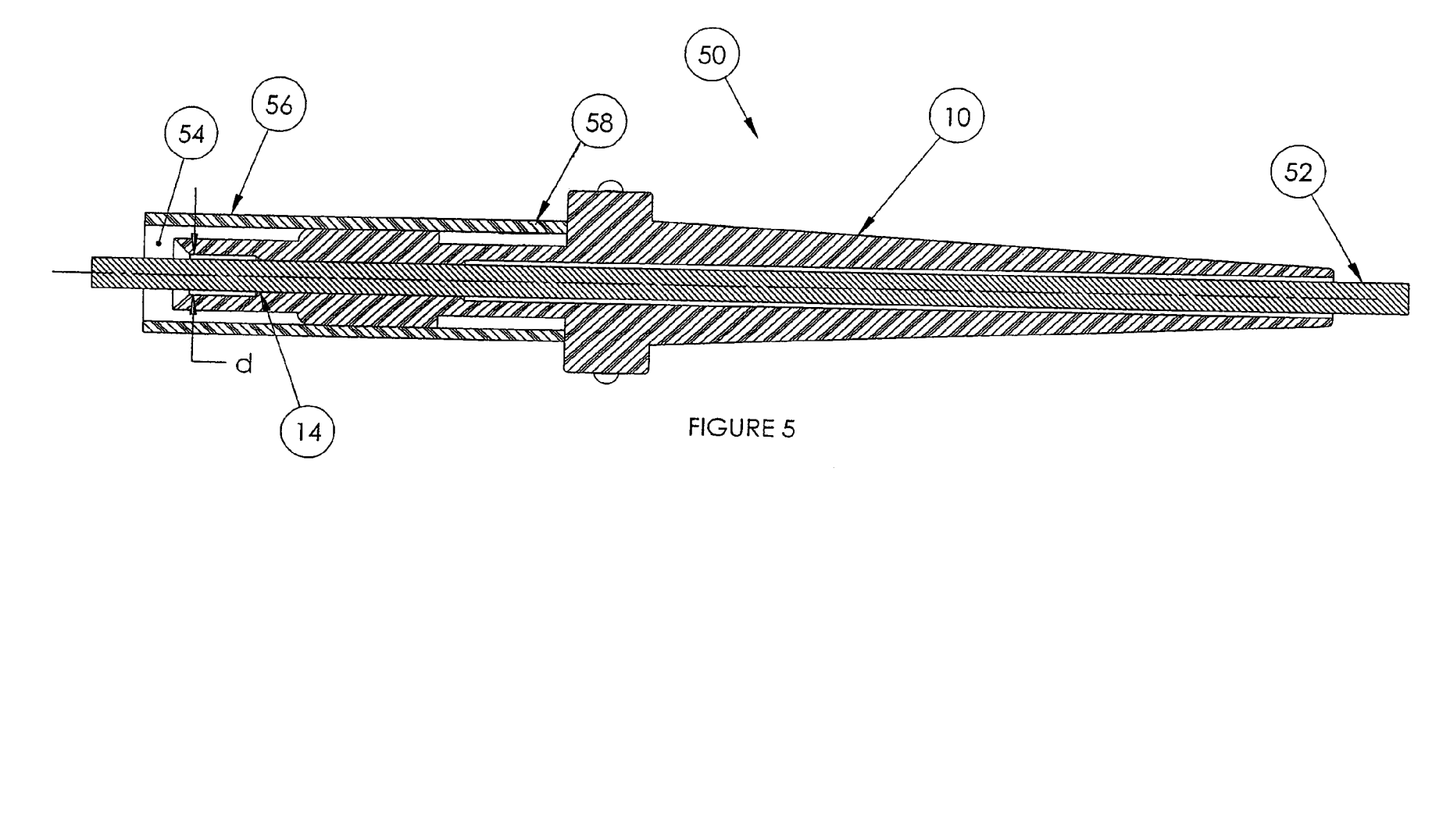
FIG. 5 is a sectional view of the catheter guidewire assembly taken along line 5-5 of FIG. 4.

A guidewire assembly 50 incorporating the guidewire straightener 10 of the present invention is shown in FIGS. 4 and 5. The guidewire assembly 50 is comprised of a guidewire 52 disposed within a tube passageway 54 of a guidewire tube 56. The guidewire 52 has a "J-shaped" distal end 53. The tube passageway 54 has an inner diameter "d". The guidewire tube 56 is connected to the proximal end 14 of the guidewire straightener 10.

The guidewire tube 56 is preferably coiled as shown for the ease of the user. The guidewire 52 is typically approximately 24 inches (61 cm) long and, by coiling the guidewire 52 along with the guidewire tube 56, the user can more readily handle the guidewire 52 and advance the guidewire 52 into the patient.

The guidewire tube 56 includes an open distal end 58, through which the guidewire 52 is advanced, the distal end 58 having a collar with an inner diameter larger than tube passageway diameter "d". The distal end 58 of the guidewire tube 56 is inserted over the proximal end 14 of the guidewire straightener 10, so that the distal end 58 of the guidewire tube 56 and the proximal end of the guidewire straightener 10 engage each other with a press fit.

The diameter "D" of the lugs 24 is larger than the diameter "d" of the tube passageway 54 so that, as is seen in FIG. 5, the distal end collar of guidewire tube 56 biases the lugs 24 and the biasing members 26 into the straightener passageway 18. Each lug 24 biases its respective biasing member 26 against the guidewire 52 so that the guidewire 52 is longitudinally engaged along a length of the guidewire 52 by the biasing members 26. The biasing members 26, in turn, bias the lugs 24 against the tube's collar to releasably retain the straightener 10 in the tube 56.

Figure 6:
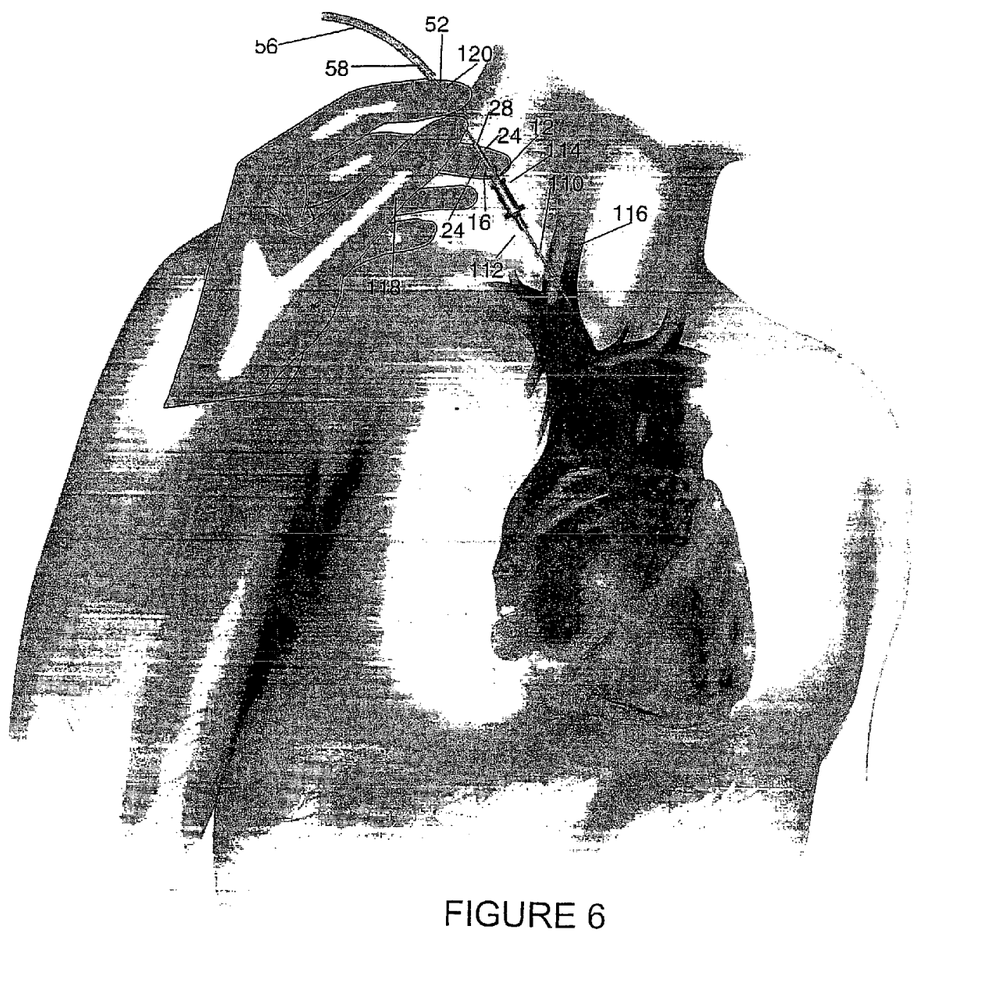
FIG. 6 is a schematic view showing operation of the catheter guidewire assembly during insertion of a guidewire into a patient.

Referring now to the guidewire insertion procedure of FIG. 6 during a catheter insertion procedure, an incision 110 is initially made near an insertion site 112 which is to be aspirated with a syringe or other introducer apparatus near or proximate the area to be catheterized. If the catheter is used for hemodialysis and the area to be catheterized is the internal jugular vein 116, the incision 110 is made in the clavicular triangle region, as shown for example, in FIG. 6. The exact location of the incision 110 can be varied by the physician. In accordance with the Seldinger technique, a narrow needle 114 connected to the syringe is inserted through the incision 110 and into the vein 116, and the vein 116 is aspirated. The syringe is disconnected from the needle 114, leaving the needle 114 in the vein 116.

The guidewire 52 is next inserted into the vein 116 through the needle 114. To insert the guidewire 52 into the vein 116, the proximal end 14 of the straightener 10 is removed from the tube 56. The biasing members 26 bias away from the straightener passageway 18, releasing the guidewire 52 from between the biasing members 26. The distal end 53 (see FIGS. 4 and 5) of the guidewire 52 is then retracted into the straightener 10 so that the "J-shaped" distal end 53 of the guidewire 52 is disposed within the straightener 10. The distal end 12 of the straightener 10 is then inserted into the proximal end of the needle 114. The preferably frusto-conical shape of the distal end 12 facilitates insertion of the distal end 12 into the needle 114.

Using thumb 118 and forefinger 120 on the guidewire 52 between the straightener 10 and the tube 56, the physician advances the guidewire 52 through the needle 114 and into the vein 116. Once the guidewire 52 is in place, the tube 56 and the straightener 10 are removed by advancing each of the tube 56 and the straightener 10 along the guidewire 52 away from the distal end 53 of the guidewire 52 and then off the proximal end of the guidewire 52. Next, the needle 114 is removed by advancing the needle 114 along the guidewire 52 away from the distal end 53 of the guidewire 52 and then off the proximal end of the guidewire 52. A dilator (not shown) and a tearable sheath (not shown) are introduced over the guidewire 52 and partially into the vein 116. The insertion site 112 is now ready to accept a catheter assembly (not shown). At least one catheter lumen is disposed over the proximal end of the guidewire 52 and advanced toward the distal end 53 of the guidewire 52 and into the vein.

Figure 7:
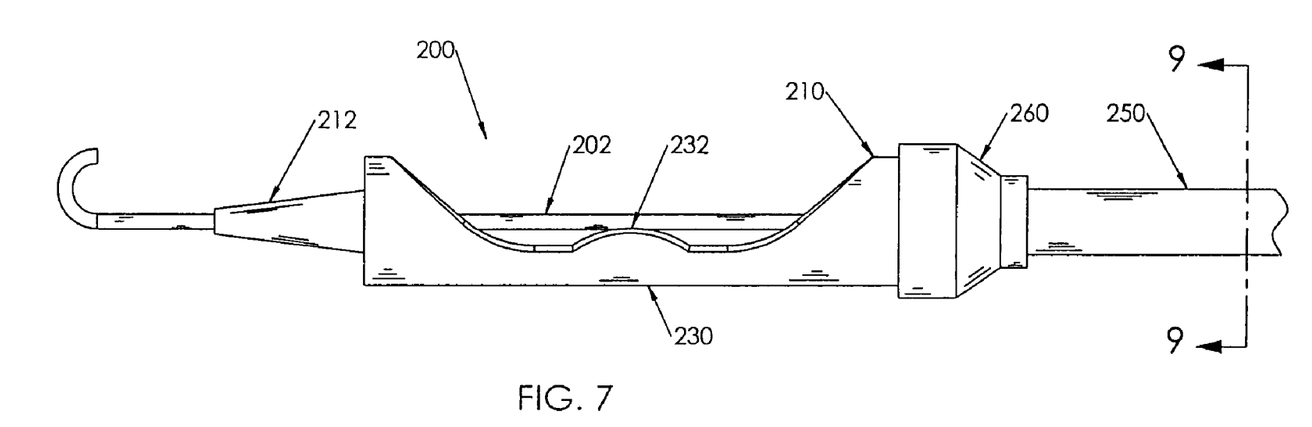
FIG. 7 is a side profile view of a catheter guidewire straightener assembly according to a second embodiment of the present invention.

An alternate embodiment of a guidewire straightener assembly 200 is shown in FIG. 7. The assembly 200 includes a straightener 210 and a guidewire tube 250. The straightener 210 is partially disposed in the tube 250 and is used to assist the inserting physician in advancing a guidewire 202 from the tube 250 during catheter insertion.

Figure 8:
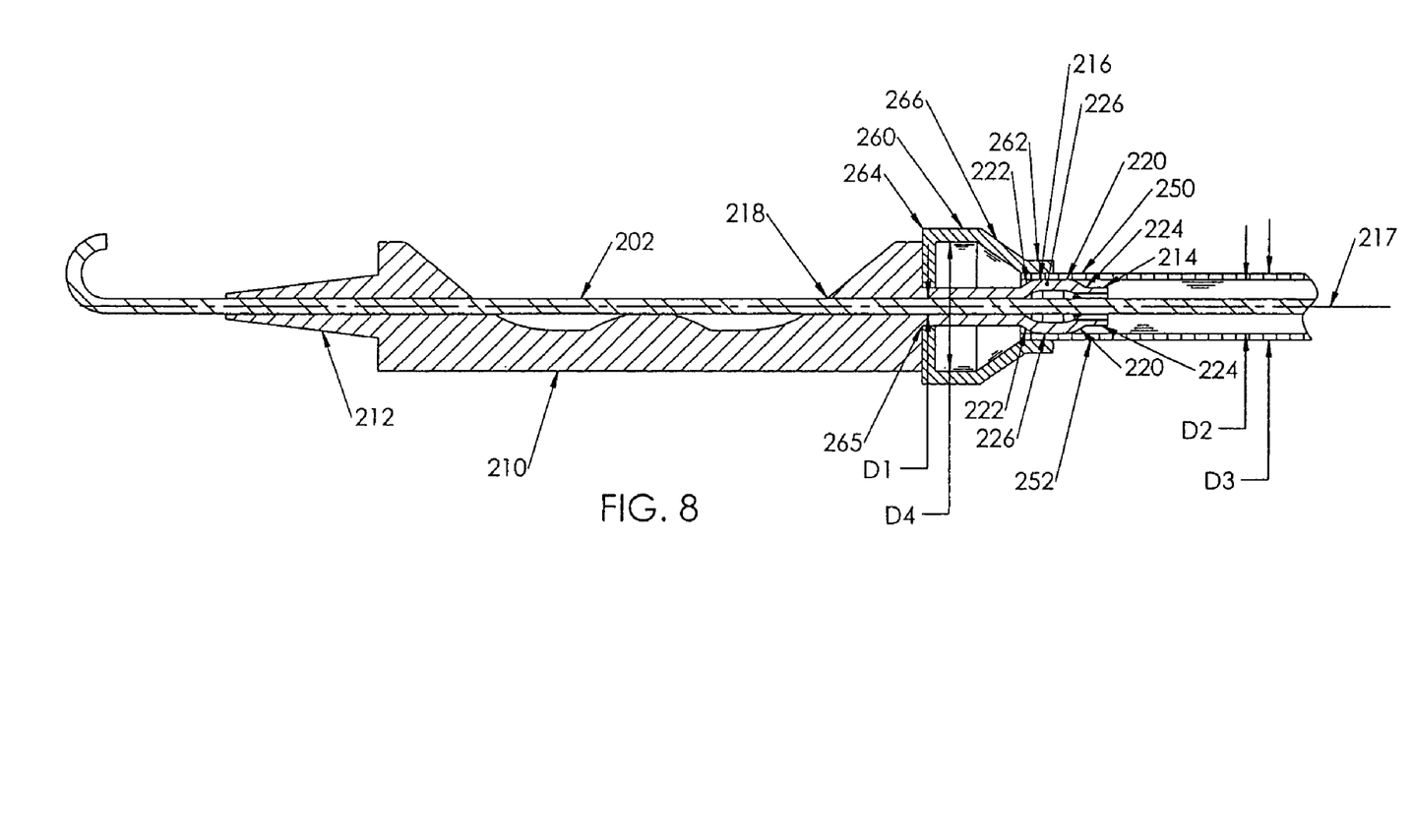
FIG. 8 is an enlarged sectional view of the guidewire straightener assembly of FIG. 7, taken along lines 8-8 of FIG. 9.

Referring to FIG. 8, the straightener 210 includes a distal end 212 that is generally conically or frusto-conically shaped. The distal end 212 is shaped to facilitate insertion of the distal end 212 into an introducer device, such as an introducer needle (not shown). The straightener 210 also includes a proximal end 214 that includes a biasing member 216. A longitudinal axis 217 extends through the straightener 210. A straightener passageway 218 extends along the longitudinal axis 217 through the straightener 210 between the distal end 212 and the proximal end 214. The passageway 218 has a diameter $D_1$ that is sized to allow the guidewire 202 to be able to be translated therethrough with a minimal force during insertion of the guidewire 202 into the patient.

Figure 9:
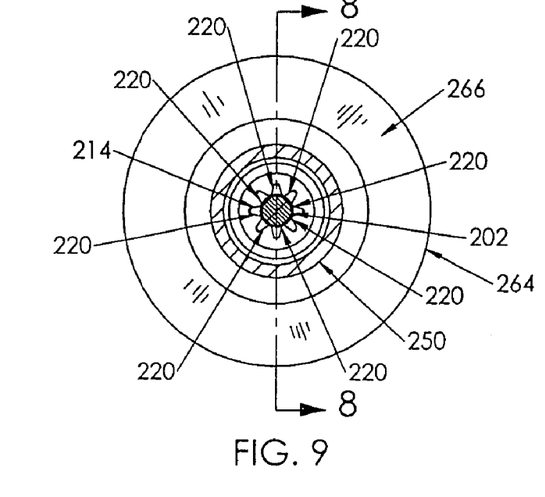
FIG. 9 is an enlarged sectional view of the guidewire straightener assembly of FIG. 7, taken along lines 9-9 thereof.

The biasing member 216 includes a plurality of fingers 220 that extend in a proximal direction. While eight fingers 220 are shown in FIG. 9, those skilled in the art will recognize that more or less than eight fingers 220 may be used. Each finger 220 has a connected end 222 that is connected to the proximal end 214 and a free end 224 that freely extends away from the proximal end 214. Each finger 220 has a body portion 226 between the connected end 222 and the free end 224 that is biased away from the longitudinal axis 217. The biasing member 216 is dimensioned such that, when the biasing member 216 is disposed within the guidewire tube 250, the interior wall of the guidewire tube 250 biases the biasing member 216 against the guidewire 202.

The guidewire advancer 210 also includes a generally elongated portion 230 that extends between the distal end 212 and the proximal end 214. The generally elongated portion 230 extends below the guidewire 202 and is open so that the guidewire 202 is accessible. A generally convex raised portion 232 extends from the generally elongated portion 230 and provides a thumb rest for advancing the guidewire 202 distally through the advancer 210.

The guidewire tube 250 includes a distal end 252 that engages the straightener 210. The guidewire tube 250 has an inner diameter $D_2$ that is sized to allow the proximal end 214 of the straightener 210 to be inserted into the guidewire tube 250. The guidewire tube 250 also has an outer diameter $D_3$. A cylindrical collar 260 is fixedly connected to the distal end 252 of the tube 250.

The collar 260 is preferably constructed from a polymer, such as polypropylene, or some other suitable material. Those skilled in the art will recognize that the collar 260 may be a separate piece from the tube 250, or the collar 260 may be integrally formed with the tube 250. If the collar 260 is a separate piece from the tube 250, the collar 260 is fixedly connected to the tube 250 by known methods, such as by an adhesive, by ultrasonic welding, or other means known in the art for connecting the collar 260 to the tube 250.

The collar 260 includes a proximal collar end 262 that fits over the exterior of the distal end 252 of the tube 250. The collar 260 also includes a distal collar end 264 that has an inner diameter $D_4$ that is larger than the outer diameter $D_3$ of the tube 250. The distal collar end 264 includes an opening 265 along the longitudinal axis 217 that is sized to allow the proximal end 214 of the straightener 210 to be inserted into the opening 265. The inner diameter $D_4$ of the distal collar end 264 is sufficiently large to allow the biasing member 216 to expand within the interior of the distal collar end 264 to allow the biasing member 216 to expand and release the guidewire 202. However, it is preferred that the distal opening 265 is sufficiently small such that the biasing member 216 cannot be easily pulled through the distal opening 265 and out of the collar 260.

The collar 260 also includes a tapered portion 266 that tapers from the proximal collar end 262, outward to the distal collar end 264. Preferably, the tapered portion 266 begins at the distal end 252 of the tube 250, although those skilled in the art will recognize that the tapered portion 266 may begin either proximally or distally of the distal end 252 of the tube 250.

The assembly 200 is provided with the straightener 210 fully inserted into the tube 250, as shown in FIGS. 7 and 8. In use, the straightener 210 is partially removed from the tube 250 by advancing the straightener 210 in a distal direction relative to the tube 250. The biasing means 216 moves distally from the interior of the tube 250 to the interior of the collar 260 to the position shown in FIG. 10. When the plurality of fingers 220 enter the interior of the collar 260, the fingers 220 spring away from the guidewire 202, allowing the guidewire 202 to be freely advanced from the distal end 212 of the straightener 210 according to known methods. The straightener 210, however, is not sufficiently moved relative to the tube 250 so as to pull the proximal end 214 of the straightener 210 through the distal opening 265 of the collar 260.

Figure 10:
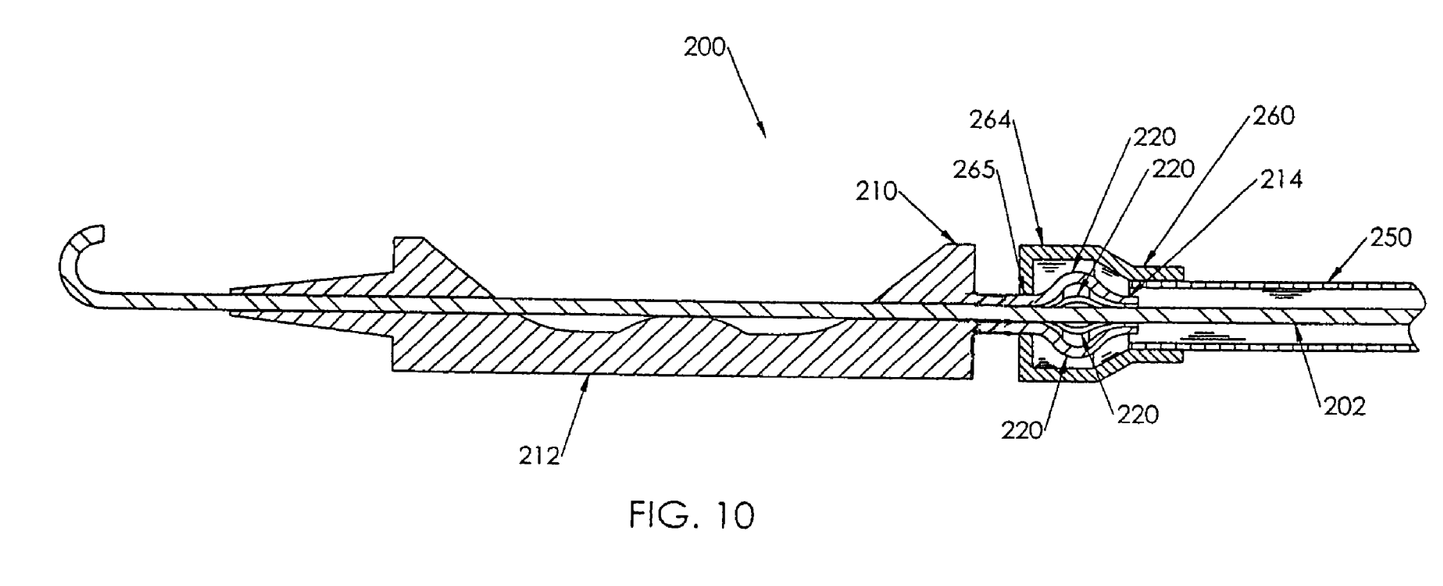
FIG. 10 is an enlarged sectional view of the guidewire straightener assembly of FIG. 7, with the guidewire straightener removed from the guidewire tube.

After the guidewire 202 is inserted a desired distance into the patient, the guidewire straightener assembly 200 is removed from the guidewire 202 by sliding the assembly 200 proximally along the guidewire 202 until the guidewire 202 exits the assembly 200. The assembly 200 is discarded and the catheter insertion procedure continues according to steps and processes well known in the art.

Figure 11:
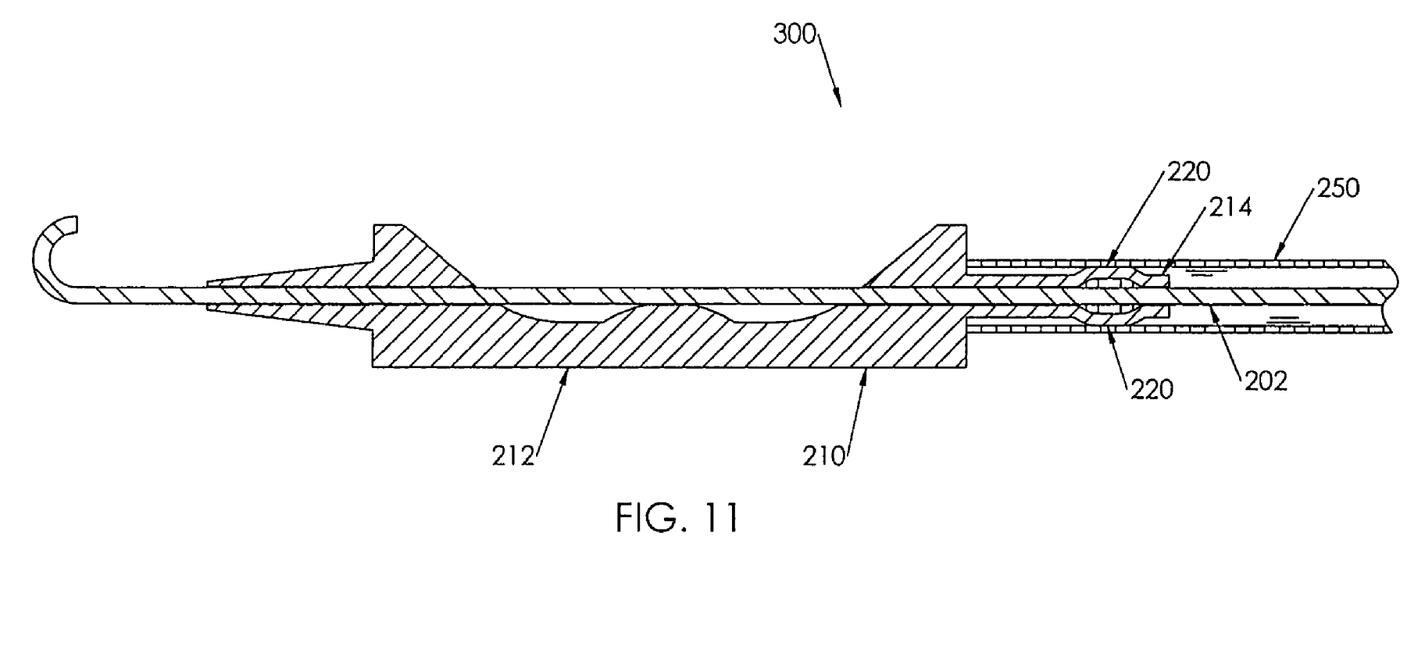
FIG. 11 is a sectional view of a catheter guidewire straightener assembly according to a third embodiment of the present invention.

While the guidewire assembly 200 with the collar 260 fixed to the distal end 252 of the tube 250 is preferred, those skilled in the art will recognize that a guidewire assembly 300, shown in FIG. 11, that omits the collar may be used. The straightener 210 is inserted into the tube 250 as shown in FIG. 11, with the fingers 220 biased against the guidewire 202.

Figure 12:
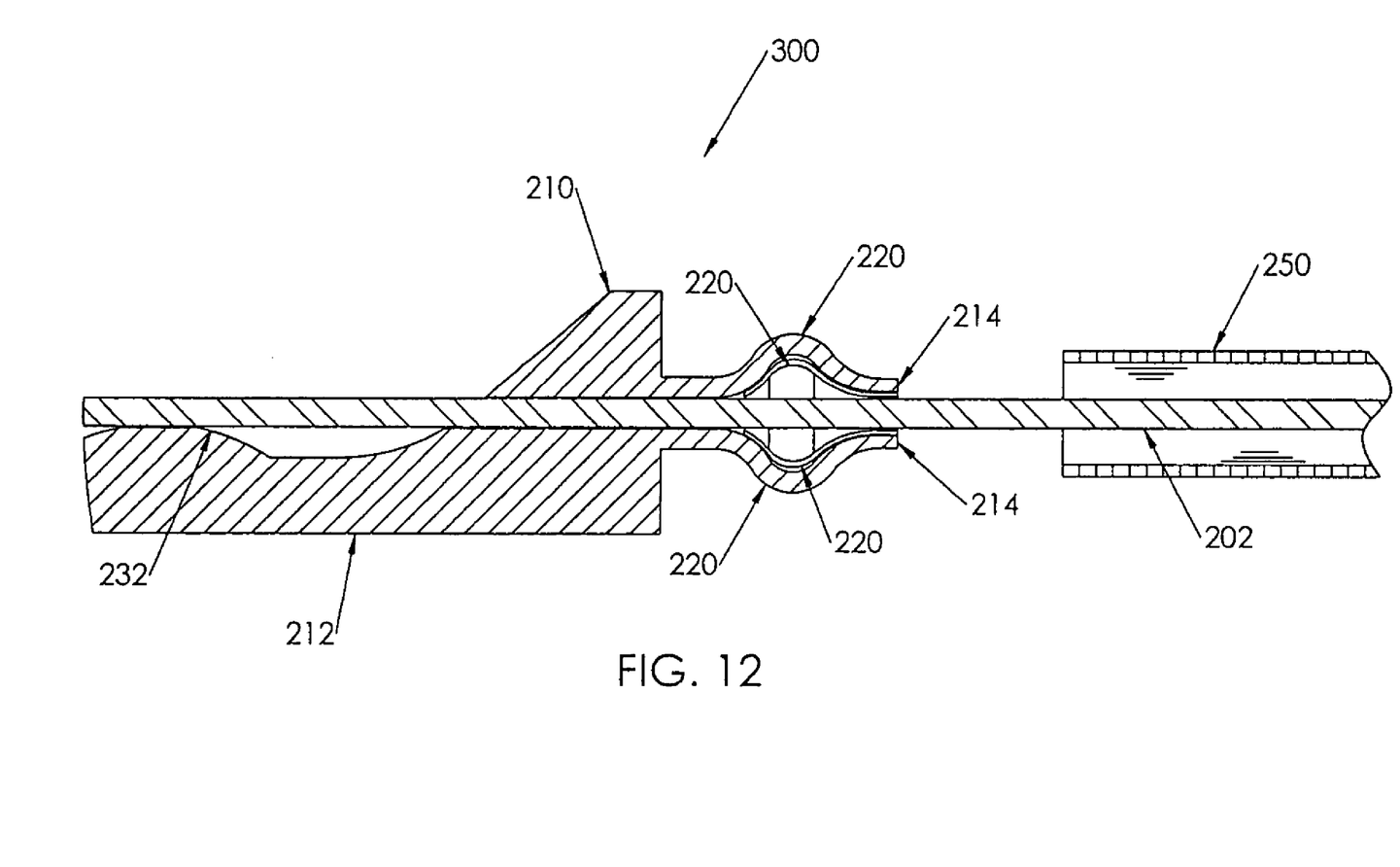
FIG. 12 is a sectional view of the catheter guidewire straightener assembly shown in FIG. 11, with the guidewire straightener removed from the guidewire tube.

In use, the straightener 210 is advanced distally with respect to the tube 250 until the proximal end 214 of the straightener 210 is removed from the tube, as show in FIG. 12. The fingers 220 spring away from the guidewire 202, allowing the guidewire 202 to be freely advanced from the distal end 212 of the straightener 210. The user biases the guidewire 202 against the generally convex raised portion 232 and advances his/her thumb in a distal direction, using friction to distally advance the guidewire 202 as well.

After the guidewire 202 is inserted a desired distance into the patient, the guidewire straightener assembly 300 is removed from the guidewire 202 by sliding the assembly 300 proximally along the guidewire 202 until the guidewire 202 exits the assembly 200. The assembly 300 is discarded and the catheter insertion procedure continues according to steps and processes well known in the art.

Figure 13:
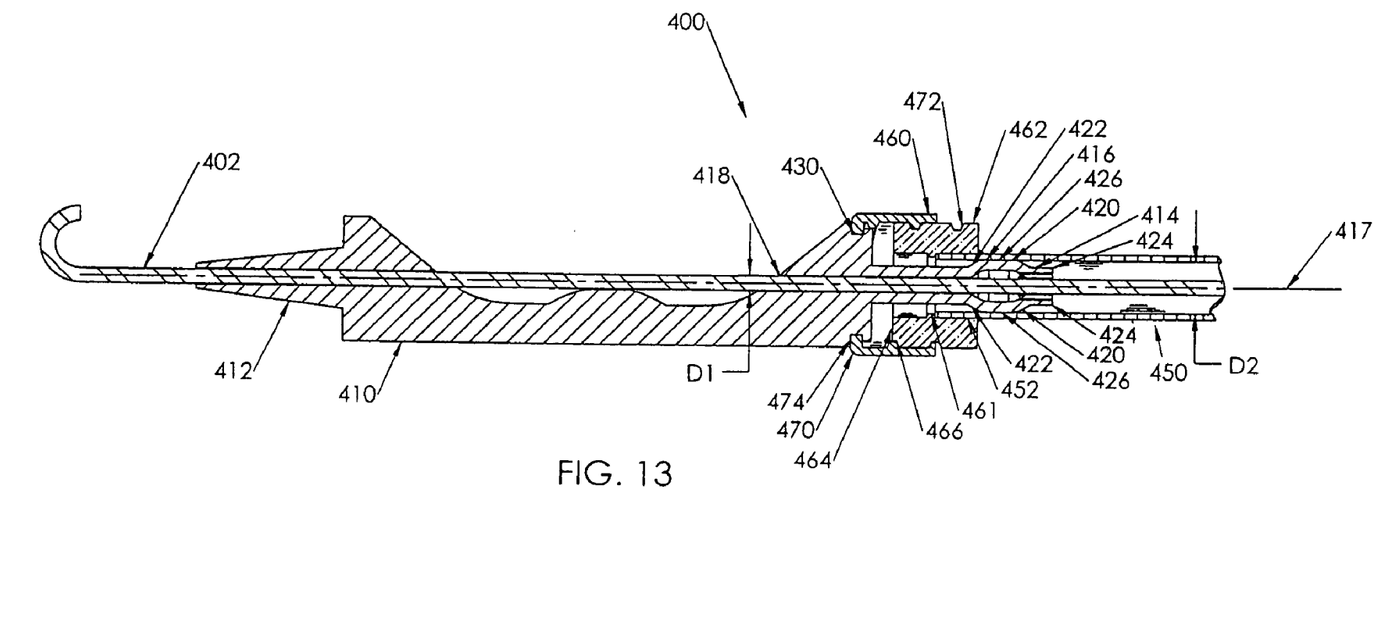
FIG. 13 is a sectional view of a guidewire straightener assembly according to a fourth embodiment of the present invention.
Figure 14:
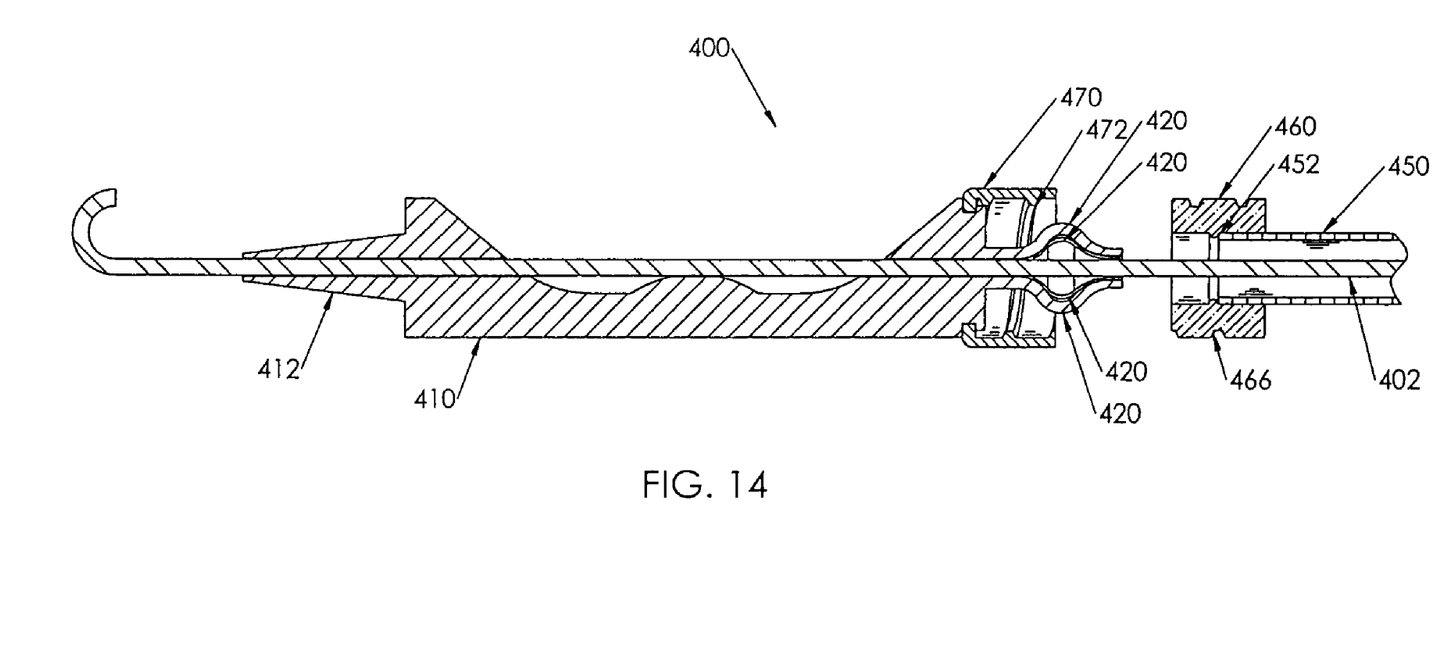
FIG. 14 is a sectional view of the guidewire straightener assembly of FIG. 13, with the guidewire straightener disconnected from the guidewire tube.

Yet another embodiment of the present invention is shown in FIGS. 13 and 14. A guidewire straightener assembly 400 includes a guidewire straightener 410 and a guidewire tube 450 that are used to retain and dispense a guidewire 402. A swivel lock assembly 460 releasably connects the straightener 410 and the tube 450 to each other.

The straightener 410 includes a distal end 412 that is generally conically or frusto-conically shaped. The distal end 412 is shaped to facilitate insertion of the distal end 412 into an introducer device, such as an introducer needle (not shown). The straightener 410 also includes a proximal end 414 that includes a biasing member 416. A longitudinal axis 417 extends through the straightener 410. A straightener passageway 418 extends along the longitudinal axis 417 through the straightener 410 between the distal end 412 and the proximal end 414. The passageway 418 has a diameter $D_1$ that is sized to allow the guidewire 402 to be able to be translated therethrough with a minimal force during insertion of the guidewire 402 into the patient.

The biasing member 416 includes a plurality of fingers 420 that extend in a proximal direction. Similar to the biasing member 216 described above and shown in FIG. 9, the biasing member 416 preferably includes six fingers 420. While six fingers 420 are preferred, those skilled in the art will recognize that more or less than six fingers 420 may be used. Each finger 420 has a proximal end 422 that is connected to the proximal end 414 and a distal end 424 that extends away from the proximal end 414. Each finger 420 has a body portion 426 between the proximal end 422 and the distal end 424 that is biased away from the longitudinal axis 417. The biasing member 416 is dimensioned such that, when the biasing member 416 is disposed within the guidewire tube 450, the interior wall of the guidewire tube 450 biases the biasing member 416 against the guidewire 402, restricting the movement of the guidewire 402 within the tube 450.

The biasing member 416 includes a plurality of fingers 420 that extend in a proximal direction. Similar to the biasing member 216 described above and shown in FIG. 9, the biasing member 416 preferably includes six fingers 420. While six fingers 420 are preferred, those skilled in the art will recognize that more or less than six fingers 420 may be used. Each finger 420 has a proximal end 422 that is connected to the proximal end 414 and a distal end 424 that extends away from the proximal end 414. Each finger 420 has a body portion 426 between the proximal end 422 and the distal end 424 that is biased away from the longitudinal axis 417. The biasing member 416 is dimensioned such that, when the biasing member 416 is disposed within the guidewire tube 450, the interior wall of the guidewire tube 450 biases the biasing member 416 against the guidewire 402, restricting the movement of the guidewire 402 within the tube 450.

The straightener 410 includes an annular groove 430 disposed between the distal end 412 and the proximal end 414. The groove 430 is sized and shaped to allow the distal end of the swivel lock assembly 460 to be rotatably attached to the straightener 410, as will be described more in detail later herein.

The guidewire tube 450 includes a distal end 452 that engages the straightener 410. The guidewire tube 450 has an inner diameter $D_2$ that is sized to allow the proximal end 414 of the straightener 410 to be inserted into the guidewire tube 450. The guidewire tube 450 also has an outer diameter $D_3$. The swivel lock assembly 460 includes a cylindrical collar 462 that is fixedly connected to the distal end 452 of the tube 450 and a swivel lock 470 that is rotatably connected to the straightener 410.

The collar 462 is preferably constructed from a polymer, such as polypropylene, or some other suitable material. Those skilled in the art will recognize that the collar 462 may be a separate piece from the tube 450, or the collar 462 may be integrally formed with the tube 450. If the collar 462 is a separate piece from the tube 450, the collar 462 is fixedly connected to the tube 450 by known methods, such as by an adhesive, by ultrasonic welding, or other means known in the art for connecting the collar 462 to the tube 450. Preferably, the collar 462 includes a stop 461 that limits the distance that the collar 462 may be advanced over the distal end 452 of the tube 450.

The collar 462 includes a distal collar end 464 that includes male threads 466. The swivel lock 470 includes female threads 472 that threadingly engage with the male threads 466. A distal end of the swivel lock 470 includes a lip 474 that rotates within the groove 430 in the straightener 410 to allow the swivel lock 470 to rotate about the longitudinal axis 417 with respect to the straightener 410.

The assembly 400 is provided with the straightener 410 fully inserted into the tube 450 and the swivel lock 470 connected to the collar 462, as shown in FIG. 13. In use, the straightener 410 is removed from the tube 450 by rotating the swivel lock 470 relative to the collar 462 and unthreading the female threads 472 from the male threads 466. When the swivel lock 470 is unthreaded from the collar 462, the straightener 410 is advanced in a distal direction relative to the tube 450. The biasing means 416 moves distally from the interior of the tube 450 to the position shown in FIG. 14. When the plurality of fingers 420 exits the distal end 452 of the tube 450, the fingers 420 spring away from the guidewire 402, allowing the guidewire 402 to be freely advanced from the distal end 412 of the straightener 410 according to known methods.

After the guidewire 402 is inserted a desired distance into the patient, the guidewire straightener assembly 400 is removed from the guidewire 402 by sliding the assembly 400 proximally along the guidewire 402 until the guidewire 402 exits the assembly 400. The assembly 400 is discarded and the catheter insertion procedure continues according to steps and processes well known in the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A guidewire straightener assembly comprising:
    a guidewire tube including:
        a tubular passage sized to accept a guidewire and having a distal end;
    and wherein the guidewire tube includes a collar at its distal end, wherein the collar comprises a longitudinal opening having a diameter larger than the diameter of a guidewire straightener proximal end,
    the guidewire straightener including:
        a distal end;
        a proximal end having an exterior surface sized to fit within the guidewire tube distal end wherein the proximal end of the guidewire straightener further includes a biasing member with at least one finger extending proximal from the proximal end to enter the guidewire tube distal end; and
        a longitudinal passageway having a diameter sized to accept the guidewire, the passageway extending between the proximal end and the distal end; and
    a guidewire disposed within the tubular passage and the longitudinal passageway; such that, when the guidewire straightener proximal end is disposed within the guidewire tube in a first position in the tubular passage, the at least one finger is biased by the tubular passage into frictional engagement with the guidewire, and, when the guidewire straightener proximal end is disposed in a second, more distal position with respect to the guidewire tube, the at least one finger is disposed within the guidewire tube distal end, and away from frictional engagement with the guidewire.

2. The guidewire straightener assembly according to claim 1, wherein the at least one finger comprises a plurality of fingers.

3. The guidewire straightener assembly according to claim 1, wherein the distal end of the guidewire straightener has a generally conical shape.

4. The guidewire straightener assembly according to claim 1, wherein, when the guidewire straightener is in its second, more distal position, its biasing member is spaced distally of the guidewire tube distal end.

5. The guidewire straightener assembly according to claim 1, wherein, when the guidewire straightener is in its second, more distal position, its biasing member is disposed within a recess of the collar sufficiently large to enable the biasing member to be essentially free of biasing engagement with an interior surface thereof.

6. A method of inserting a guidewire into a patient comprising:
   providing the guidewire straightener assembly of claim 1;
   distally disposing the guidewire straightener from the distal end of the tube such that the at least one finger is translated from the tubular passage to the collar such that the at least one finger is biased away from the guidewire;
   inserting the proximal end of the guidewire straightener into an introducer device; and
   advancing the guidewire distally through the introducer device and into the patient.

7. The method according to claim 6, further comprising, after inserting the guidewire into the patient a desired length, removing the guidewire straightener and the guidewire tube from the guidewire by sliding the guidewire straightener and the guidewire tube proximally along the guidewire.

8. A method of inserting a guidewire into a patient comprising:
   providing the guidewire straightener assembly of claim 1;
   distally disposing the guidewire straightener from the distal end of the tube with a force sufficient to move the at least one finger from the tubular passage and into the collar, but not sufficient so as to remove the at least one finger from the collar;
   inserting the proximal end of the guidewire straightener into an introducer device; and
   advancing the guidewire distally through the introducer device and into the patient.

9. The method according to claim 8, further comprising, after inserting the guidewire into the patient a desired length, removing the guidewire straightener and the guidewire tube from the guidewire by sliding the guidewire straightener and the guidewire tube proximally along the guidewire.

* * * * *